United States Patent
Yon et al.

(10) Patent No.: US 10,603,520 B2
(45) Date of Patent: Mar. 31, 2020

(54) THERAPEUTIC TREATMENT DEVICE

(71) Applicant: THERACLION SA, Malakoff (FR)

(72) Inventors: Sylvain Yon, Bagneux (FR); Francois Lacoste, Gentilly (FR); Jérémie Anquez, Paris (FR); Anthony Grisey, Meudon (FR)

(73) Assignee: THERACLION SA, Malakoff (FR)

( * ) Notice: Subject to any disclaimer, the term of this patent is extended or adjusted under 35 U.S.C. 154(b) by 520 days.

(21) Appl. No.: 15/321,208

(22) PCT Filed: Jun. 30, 2015

(86) PCT No.: PCT/EP2015/064870
§ 371 (c)(1),
(2) Date: Dec. 22, 2016

(87) PCT Pub. No.: WO2016/001238
PCT Pub. Date: Jan. 7, 2016

(65) Prior Publication Data
US 2017/0151448 A1    Jun. 1, 2017

(30) Foreign Application Priority Data
Jul. 2, 2014 (EP) .................................... 14175460

(51) Int. Cl.
*A61N 7/02* (2006.01)
*A61N 7/00* (2006.01)
*A61B 90/00* (2016.01)

(52) U.S. Cl.
CPC .......... *A61N 7/02* (2013.01); *A61B 2090/378* (2016.02); *A61N 2007/0056* (2013.01); *A61N 2007/0065* (2013.01)

(58) Field of Classification Search
None
See application file for complete search history.

(56) References Cited

U.S. PATENT DOCUMENTS

| 4,586,512 A | 5/1986 | Do-Huu et al. |
| 6,516,211 B1 | 2/2003 | Acker et al. |
(Continued)

FOREIGN PATENT DOCUMENTS

| EP | 2 532 387 A1 | 12/2012 |
| WO | 2013/135801 A1 | 9/2013 |

OTHER PUBLICATIONS

Salomir, Rares et al., "Local Hyperthermia with MR-Guided Focused Ultrasound: Spiral Trajectory of the Focal Point Optimized for Temperature Uniformity in the Target Region", Journal of Magnetic Resonance Imaging, 2000, pp. 571-583, vol. 12, Wiley-Liss, Inc.
(Continued)

*Primary Examiner* — Brian T Gedeon
(74) *Attorney, Agent, or Firm* — Davis & Bujold PLLC; Michael J. Bujold

(57) ABSTRACT

A device for therapeutic treatment which comprises a HIFU transducer for generating and transmitting HIFU pulses to a target. The HIFU transducer is operable in at least a probing mode, during a probing phase, and in a treatment mode, during a treatment phase. In the probing phase the HIFU transducer is operated with at least one probing operation characteristic. The probing operation characteristic includes emission of a pulse with a focal point. During the treatment phase, the HIFU transducer operates with at least one treatment operation characteristic different from the probing operation characteristic. The device further comprises a detector designed to detect a change of tissue properties caused by the HIFU pulses in the target during the probing phase. The device further comprises a computer or microprocessor for determining at least one probing parameter necessary to achieve the change of tissue properties detected by the detector during the probing phase.

19 Claims, 6 Drawing Sheets

(56) References Cited

U.S. PATENT DOCUMENTS

Figure 1:
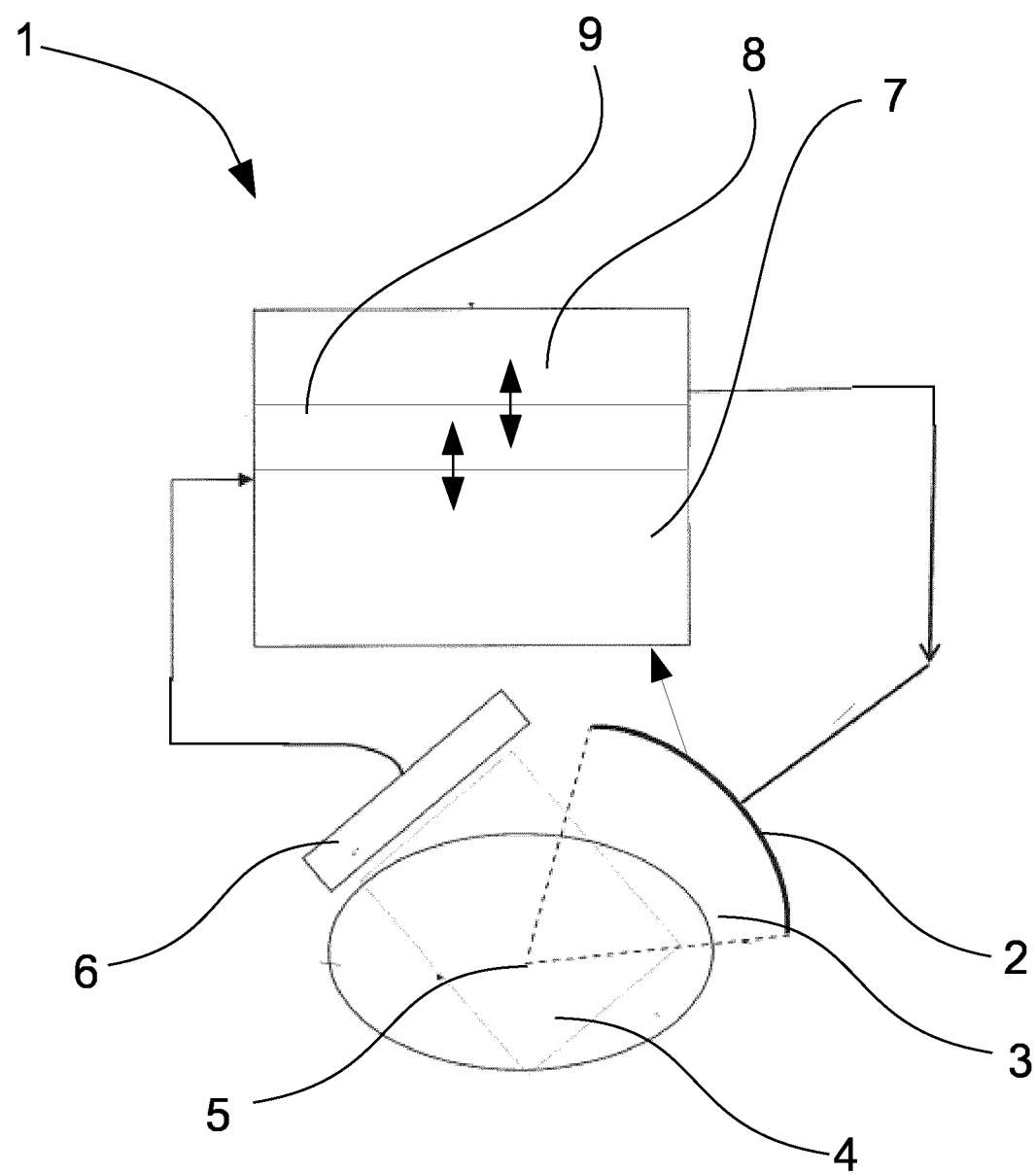

2007/0088346 A1  4/2007  Mirizzi et al.
2008/0114274 A1  5/2008  Moonen et al.
2009/0171185 A1  7/2009  Chou et al.
2010/0036292 A1  2/2010  Darlington et al.

OTHER PUBLICATIONS

Sanghvi, N.T. et al., "New Developments in Therapeutic Ultrasound", IEEE Engineering in Medicine and Biology, Nov./Dec. 1996, pp. 83-92.
Chapman, Alexander et al., "Thermal Ablation of Uterine Fibroids Using MR-Guided Focused Ultrasound-a Truly Non-invasive Treatment Modality", Urogenital, 2007, pp. 2505-2511, vol. 17, Eur Radial.
European Search Report Corresponding to 14175460.6 dated Dec. 15, 2014.
Invitation to Pay Additional Fees Corresponding to PCT/EP2015/064870 dated Sep. 29, 2015.
International Search Report Corresponding to Corresponding to PCT/EP2015/064870 dated Dec. 10, 2015.
Written Opinion Corresponding to PCT/EP2015/064870 dated Sep. 29, 2015.

THERAPEUTIC TREATMENT DEVICE

The present invention relates to a device for therapeutic treatment, a method for controlling a therapeutic treatment, a method for treating tissue and a computer program product according to the independent claims.

In particular, the Invention concerns devices and methods for treatment with high intensity focused ultrasounds (HIFU).

Conventionally, in the HIFU treatment, an acoustic treatment transducer emits concentrated acoustic waves into a target tissue. These waves are absorbed by the tissue, which provokes a temperature rise in the tissue in the focal region. This temperature elevation in turn induces a local necrosis and thereby allows destruction of living tissue at a distance without any direct contact. Another mode of action is cavitation in which the ultrasonic field interacts with bubbles which are present, created or injected into the tissue, creating mechanical damage to that tissue. An example of such mode of action is dubbed "histoptripsy".

In most HIFU systems, a pulse and pause method is used. Therein, a beam is concentrated onto a very small focal spot on the target tissue. The beam is fixed with respect to the tissue to be treated during emission of HIFU. After a predefined pause period, the transducer is moved to another location and a new pulse is emitted.

Such concentrated beams may be disadvantageous as they can result in overtreatment around the focus, for example by bringing that area of the tissue to unnecessary high temperature. In such a case degassing or boiling may happen which may be visible by on line ultrasonic imaging. This situation is undesirable because on one hand it affects the lesion size predictability, i.e. healthy neighbouring tissue might be affected. On the other hand acoustic energy is wasted on a tissue which is already dead, resulting in unnecessary long treatment durations.

One of the main challenges associated with the HIFU technique is the control of the temperature increase and of the size of the lesion created with this technique. Among the possibilities for control some device implement MRI imaging, which allows a direct visualization of the temperature in the treated area. Those MRI systems are, however, expensive and lead to high treatment costs.

It has been proposed (see e.g. Local hyperthermia with MR-guided focused ultrasound: Spiral trajectory of the focal point optimized for temperature uniformity in the target region; Journal of Magnetic Resonance Imaging, 12:571-583) to create thermal lesions by a single pulse following a spiral trajectory. The volume of tissue killed per second increases along the pulse, because of thermal build up, i.e. pre-heating of the surrounding tissue. One of the main problems is the control of the created lesion in terms of size and position, particularly in the absence of direct temperature measurement of the tissue.

US 2008/0114274 A1 proposes to use MRI imaging for temperature measurement and move the focal point on a predetermined trajectory. Such a movement leads to a spatial distribution of temperature. During the movement the temperature is measured with the MRI imaging probe.

As stated above, such MRI systems are expensive and lead to high treatment costs. Further, in such a system, the distribution of heat is only achieved through movement of the focal point, leading to limited options of heat distribution and adaption to different target features.

It is an object of the present invention to prevent the disadvantages of the prior art, in particular, to provide a device and method which provide a reliable, cheap and adaptive control of created lesions.

The object is achieved by a device, methods and a program according to the independent claims.

In particular, the object is achieved with a device for therapeutic treatment comprising the following components: a HIFU transducer is provided for generating and transmitting HIFU pulses to a target. The HIFU transducer is operable in at least a probing mode during a probing phase and in a treatment mode during a treatment phase. In the probing phase, the HIFU transducer is operated with at least one probing operation characteristic. The probing operation characteristic includes emission of a pulse with a focal point. In the treatment phase, the HIFU transducer is operated with at least one treatment operation characteristic different from the probing operation characteristic. The HIFU transducer may be composed of several transducers. Preferably these transducers share a common focus. The HIFU transducer may also be made of multi-elements.

The device further comprises a detector designed to detect a change of tissue properties caused by said HIFU pulses in the target during said probing phase.

The device further comprises calculating means such as a computer or a microprocessor for determining at least one probing parameter necessary to achieve said change of tissue properties detected by the detector during the probing phase.

Further, a control for defining said treatment parameters on the basis of said probing parameters is provided.

The control is further designed to change the operation characteristics from the probing phase to the treatment phase by increasing an area on the target of at least one unitary lesion impinged by said HIFU pulse during the treatment phase.

As used herein "operation characteristics" include "operation parameters" such as the power or duration of pulse, pause duration between pulses, but also other characteristics such as for example the focus and/or movement of the treatment transducer or the focal point, respectively. The term might also include the distance from the transducer to the target.

The detector might be an imaging probe. Alternatively or additionally, the detector might analyze the reflected signal or an interference pattern which are indicative of tissue modifications. The concept of the detection is further described in WO 2013/135801, which is incorporated herein by reference.

The detector used to detect the change of tissue properties is preferably an ultrasonic imaging probe. The detector is able to estimate some of the acoustic properties of the tissue.

An ultrasonic probe is rather inexpensive and easy to handle. Further, an ultrasonic probe is usable without further elements such as e.g. a tube and a magnetic coil for MRI imaging.

During the probing phase, the power might be increased from one pulse to another in order to achieve a change of tissue properties. It is for example possible to start with a low power pulse and increase the power from one pulse to the next until the change is detected. Additionally or alternatively, e.g. the duration of the pulses might be adjusted.

Alternatively, the power and/or duration of the pulses remain constant during the probing phase. The change can then be achieved through a thermal build-up of the tissue by applying multiple pulses.

In the present context changes of tissue properties are defined to be any sign of a change in the acoustic properties of tissue under treatment. Preferably, the changes in acoustic properties are hyperechoic marks. The change in the acoustic properties of the tissue can be broadband emissions or a spectrum of harmonics, which can occur due to cavitation. In particular hyperechoic marks are a manifestation of increased acoustic reflectivity of the tissue in the treated area, notably originating from newly created gas bubbles. Furthermore, such changes can, for example, stem from temperature increase and tissue boiling, inertial cavitation or tissue hardening. Hyperechoic marks may reflect the sudden occurrences of bubbles in the tissue, which will locally increase the reflection of incoming ultrasonic waves back to the transducer. Those reflected waves may in turn be detected by whitening on the ultrasonic image of the treated area or by a surge in the reflected electrical signal to the HIFU transducer.

When such a change of tissue properties is detected by the detector, along with its time of arrival, calculating means determine at least one, preferably all, probing parameter, which were used until the change of tissue properties was achieved. The change of tissue can be detected by the detector e.g., because of an increase in power reflection from the target or a change of an interference image.

Based on the calculated probing parameter (s), the treatment parameters are then set by control means. Preferably, at least one parameter of the treatment phase is chosen differently from the respective parameter in the probing phase.

Alternatively, the parameters during the treatment phase are the same as the parameters used in the probing phase.

The treatment phase can start directly adjoining the probing phase.

Alternatively, there is a pause between the probing phase and the treatment phase in which no HIFU pulses are transmitted. During such a pause, the tissue on the target, i.e. skin of the patient can cool. Such a cooling might add in avoidance of overtreatment, and avoid safety issues such as skin burns.

Even though the calculation of parameters is mainly achieved in the probing phase and the treatment of the target is mainly achieved in the treatment phase, calculation of parameters might also be done in the treatment phase in order to adapt the parameters for subsequent treatment, i.e. probing might further occur in the treatment phase. During the probing phase a first ablation might already occur, i.e. a first partial treatment might already occur in the probing phase.

Therewith, the parameters for the treatment phase can be set such as to e.g. avoid the occurrence of hyperechoic spots or overburning.

The operation characteristics are further changed by increasing an area on the target of at least one, preferably all, pulses impinged by the HIFU pulse during the treatment phase. Hence, the area which was impinged during the probing phase by one pulse is enlarged. The increase of the area results in a better heat distribution. Therewith, a larger target area is treated with the same amount of energy. This also means that in the same time less energy is delivered per area in the treatment phase. This avoids overburning or boiling of the target during the treatment phase.

After the treatment has been performed by e.g. executing a predefined number of pulses (e.g. ten or another number of pulses), a new probing phase might be started. Alternatively a probing phase may be started if changes are detected in the tissue during the treatment phase. Afterwards, a new treatment phase might be started. This loop might be performed until the end of treatment. Before starting a new probing phase, a pause without transmission of HIFU waves might be performed. In the pause, the target can cool.

There might also be a pause between the different pulses of the treatment phase in order to let the skin cool between the treatment pulses.

The device according to the invention allows a change from the probing characteristics to the treatment characteristics by adaption of parameters and by an increase of the treatment area during a HIFU pulse. With such a device, the treated volume in the target per used energy can be increased with respect to the ordinary legacy pulse method.

If the treatment parameters needed to achieve a change in tissue properties of the target are defined, the energy needed to achieve such a change is known. Therewith, one can adapt the characteristics such as to achieve the desired effect with the least energy and such as to avoid overtreatment. Therewith, costs linked to length of treatment are reduced and the risks associated with treatment are significantly reduced.

Preferably, the control of the device is designed to increase the area on the target impinged by said HIFU pulse by defocussing or sweeping the HIFU pulses. The calculating means and the control may be implemented by one common computer or by separated dedicated microprocessors. Based on the output of the probing phase, the control means may also decide which moving pattern or pattern size is the most appropriate for that particular treatment configuration.

By defocussing the pulse, an increased area is treated with one HIFU pulse. Therewith, less energy is delivered per time per area, which avoids overburning or boiling.

In an alternative preferred device according to the invention, the control is designed to increase the area on the target impinged by each HIFU pulse by moving said focal point during the pulse over the target.

Moving of the focal point might be achieved with mechanical or electronic means. In the case of mechanical means, a robotic system actuates the transducer preferably with 2 to 3 degrees of freedom.

Moving the focal point during the pulse achieves, similar to the defocussing, that an increased area is treated with one HIFU pulse. Therewith, less energy is delivered per time per area, which avoids overburning or boiling as already described above for the defocussing. The focal point is preferably moved in a predetermined specific pattern, i.e. along a predetermined trajectory. For example the pattern may be a circle or in the form of a daisy.

Boiling or cavitation can be used to increase the lesion size, especially along the main propagation axis during the ablation phase. This is particularly true if the transducer's f-number is small enough so that boiling or cavitation do not lead to a significant loss of precision in the lesion size.

Therefore, the focal spot trajectory might come back to the central part of the lesion to maintain boiling or cavitation in this zone and increase heat deposition. Preferably, the focus is moved across a 1 mm-circle around the trajectory center during the ablation pulse about 2 to 12 times.

Preferably, the ablation phase is designed to benefit from the energy deposited during the probing phase to increase the ablated volume. For example, in the particular case where the last probing pulse has significantly increased the tissue temperature or induced boiling and it was delivered at a neigbouring, preferably the same, location, the specific trajectory coming back to the central part can be used to benefit from the residual heat of the probing phase during the ablation phase. The central part, which preferably is in the centre of ablation pulse trajectory, has been pre-heated in the probing phase. With a trajectory airways coming back to this centre spot, the boiling at the centre will be maintained so that upcoming energy will increase the lesion size.

In the device according to the invention, the calculating means are preferably designed to detect parameters including at least one of the duration of HIFU pulses and power of HIFU pulses. The calculating means are preferably and typically formed by a computer or a microprocessor.

As already mentioned, the power per area in the treatment phase is less than in the probing phase. This is achieved through an increase of the impinged area of at least one pulse. Further, some parameters such as pulse duration and/or power might be changed from the probing phase to the treatment phase. The duration and the power define the total energy delivered per area. Measuring the duration and/or the power and a possible adaption of the measured parameter provides a simple method for reducing the power per area and hence for reducing heating.

Alternatively, the parameters calculated in the probing phase may be set substantially identically for the treatment phase and the reduction of energy delivered per area is achieved exclusively by the increase of the impinged area. Nevertheless, these parameters are preferably measured in the probing phase in order to set the (identical) parameters in the treatment phase.

Preferably, the control of the device is designed to generate HIFU pulses having a length of 2 to 8, preferably 4, seconds during the probing phase. During the pulse the detector checks for change of tissue properties. More than one short pulse might be necessary because e.g. the initial pulse power is too low. The power might be increased from one pulse to the next in order to achieve a tissue property change. Alternatively, multiple pulses with the same power might be directed to the target such that the tissue is pre-heated by forgoing pulses of the multiple pulses in order to achieve such a change in the tissue properties by the later pulses of the multiple pulses.

Additionally or alternatively, the duration of the pulse might be changed. It is also possible to use shorter or longer pulses than 2 seconds or 8 seconds, respectively.

The control is preferably further designed to generate HIFU pulses having a length of 8 to 30 or 8 to 10 and/or 10 to 30, preferably 12, seconds during the treatment phase.

The pulses during the treatment phase are therefore preferably longer than in the probing phase. During the treatment phase, the area impinged by the pulse is increased and, hence, less energy is delivered per area. Therefore, longer pulses can be delivered without resulting in an overburning or boiling but only in an ablation of the target.

It is also possible to use shorter or longer pulses than 10 seconds or 30 seconds in the treatment phase, respectively. The pulses during the treatment phase might also have the same length as the pulses in the probing phase.

Preferably, the control of the device is designed to set the power of the transducer during the treatment phase to less than 100%, preferably to about 75%, of the power of the transducer during the probing phase necessary to achieve changes of the tissue properties in the target detected by the detector.

As described above, the power during the treatment phase per area is less as compared to the probing phase in order to avoid a waste of energy because of overburning or a false estimation of the lesion size because of boiling. By setting the power of the transducer during the treatment phase to less than 100% of the power during the probing phase, overtreatment and boiling are prevented. As the pulses of the treatment phase might be longer than the pulses of the probing phase, such a reduction of power might be necessary.

Alternatively 100% of the power of the probing phase is used in the treatment phase. The avoidance of overtreatment might then be exclusively achieved through the increase of the impinged area during the treatment phase.

The invention further concerns a method for controlling a therapeutic treatment device, preferably a device as described above, comprising the steps of
    detecting changes of tissue properties caused by HIFU waves emitted by a HIFU transducer operated during a probing phase with probing operation characteristics with an detector,
    determining at least one probing parameter necessary to achieve said change of tissue properties detected by the detector during the probing phase
    defining treatment parameters for a treatment phase based on said probing parameters
    changing the operation characteristics from the probing phase to the treatment phase by increasing an area of at least one pulse on the target impinged by at least one HIFU pulse on the target during the treatment phase.

By controlling the device with this method, the energy delivered in the treatment phase per area can be reduced as compared to the energy during the probing phase which leads to a change of tissue properties. With such a method, overburning and/or hyperechoic marks and therefore, energy wasting and/or unpredictable lesion sizes can be avoided.

In the method, the area on the target impinged by said HIFU pulse is preferably increased by defocussing the HIFU pulses of the HIFU transducer.

In an alternative preferred method, the target impinged by said HIFU pulse is increased by moving the focal point of the HIFU pulses of the HIFU transducer over the target.

Moving or defocussing the HIFU pulses can also be achieved by providing an array of transducer elements, wherein each single element is specifically energized, by for example adjusting its phase with respect to the phases of the other elements of the array.

In a preferred defocussing arrangement, the transducer is set to form a toroid HIFU beam, where the beam is concentrated onto a ring focus. This may be achieved by natural focusing, i.e. the shape of the transducer is toroidal. In this case, the probing phase is carried out by electronically setting the phase of the elements of the transducer so that the HIFU beam is spherical with a center positioned in the area to be probed. In another arrangement, the transducer is spherical and the treatment phase is carried out with powering the transducer so that the emitted HIFU beam is toroidal.

Either method results in a reduction of delivered power per area on the target.

The invention further concerns a method for treating tissue with HIFU from a therapeutic treatment device, preferably a device as described above, comprising the steps of:
    Emitting HIFU waves with defined parameters with a HIFU transducer operated with probing operation characteristics during a probing phase
    detecting changes of tissue properties caused by the HIFU waves emitted with an detector,
    determining at least one probing parameter necessary to achieve said change of tissue properties detected by the detector during the probing phase
    defining treatment operation characteristics for a treatment phase based on said probing characteristic changing the operation characteristics from the probing phase to the treatment phase by increasing an area of at least one pulse on the target impinged by said HIFU pulse Emitting HIFU waves with defined parameters during said treatment phase.

In such a treatment, the energy delivered in the treatment phase per area can be reduced as compared to an energy delivered during the probing phase which leads to a detectable change of tissue properties. Therewith, overburning and/or hyperechoic marks and hence, energy wasting and/or unpredictable lesion sizes can be avoided during the treatment. The energy delivered per pulse in the treatment phase may be comparable to the energy delivered by pulse in the probing phase.

In the method, the area on the target impinged by said HIFU pulse is preferably increased by defocussing the HIFU pulses of the HIFU transducer.

In an alternative preferred method, the target impinged by said HIFU pulse is increased by moving the focal point of the HIFU pulses of the HIFU transducer over the target.

Either method results in a reduction of delivered energy per second per area on the target. The target is treated and ablation occurs without wasting energy for an overtreatment.

The invention further relates to a computer program product comprising software code portions for performing the steps of any one of the method mentioned before, when the product is run on a computer.

The program can be used in order to perform the method automatically.

Alternatively, the methods are performed manually.

The invention further relates to a device, preferably a device as described herein before. The device comprises a HIFU) transducer for generating and transmitting HIFU pulses to a target. The device further comprises a control for moving the focal point. The control is designed to move the focal point in a predefined trajectory, such that at least one point on the target is impinged more often than remaining points on the trajectory.

With such an arrangement the boiling at the at least one point is maintained as the trajectory always comes back to this specific point. Hence, the lesion size will be increased.

The invention also relates to a method for controlling a device, preferably a device as disclosed above. The method comprises the steps of generating and transmitting HIFU pulses to a target with a transducer. Further, in the method a focal point of the HIFU pulse is moved in a predefined trajectory with a control, such that at least one point on the target is impinged more often than remaining points on the trajectory.

With such a method, the boiling at the at least one point is maintained as the trajectory always comes back to this specific point. Hence, the lesion size will be increased.

The description is in the following described with reference to schematic drawings, which show non-limiting examples of the invention.

The figures show:

FIG. 1: A schematic view of a device according to the invention in the probing phase FIG. 2: A schematic view of the device according to FIG. 1 in the treatment phase.

Figure 3:
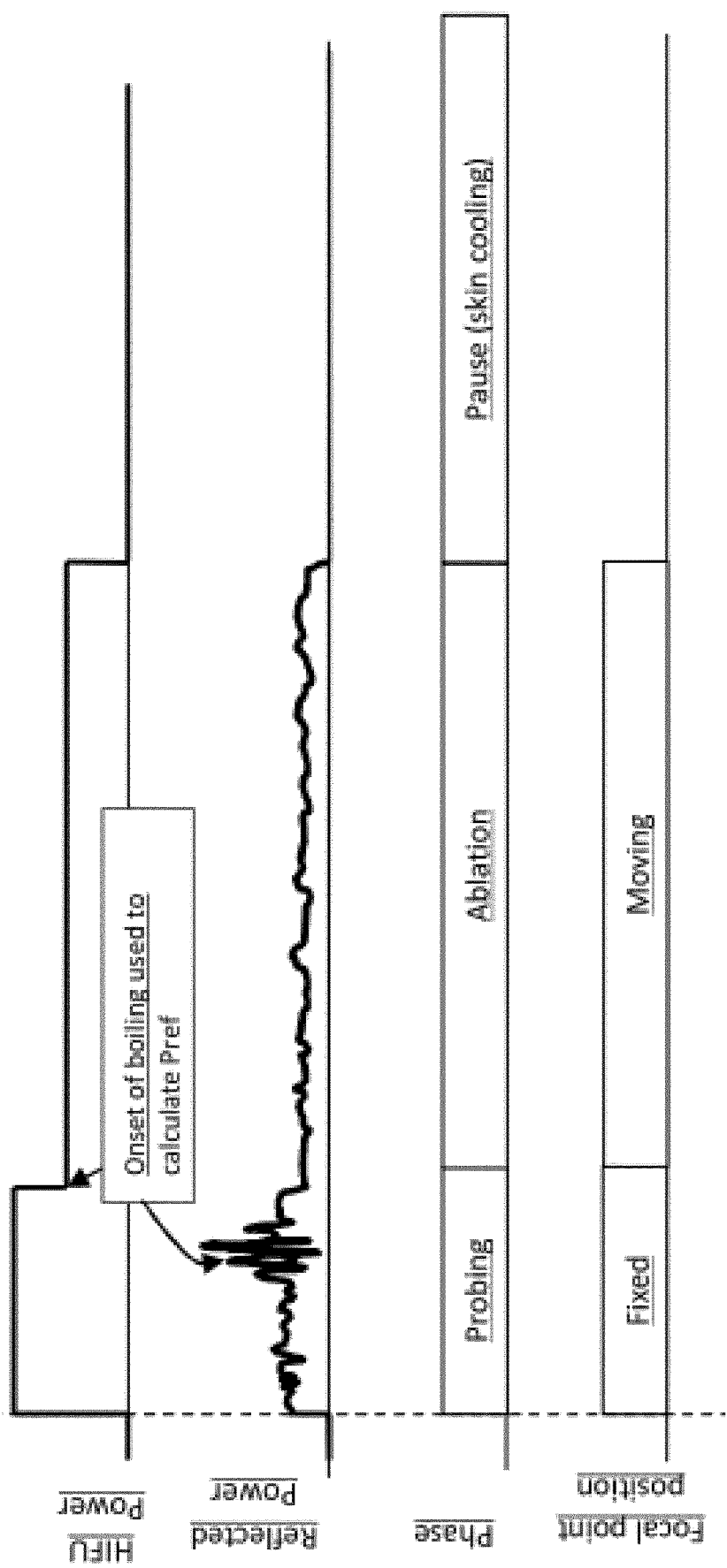

FIG. 3: A diagram of a first treatment cycle according to the invent ion.

Figure 4:
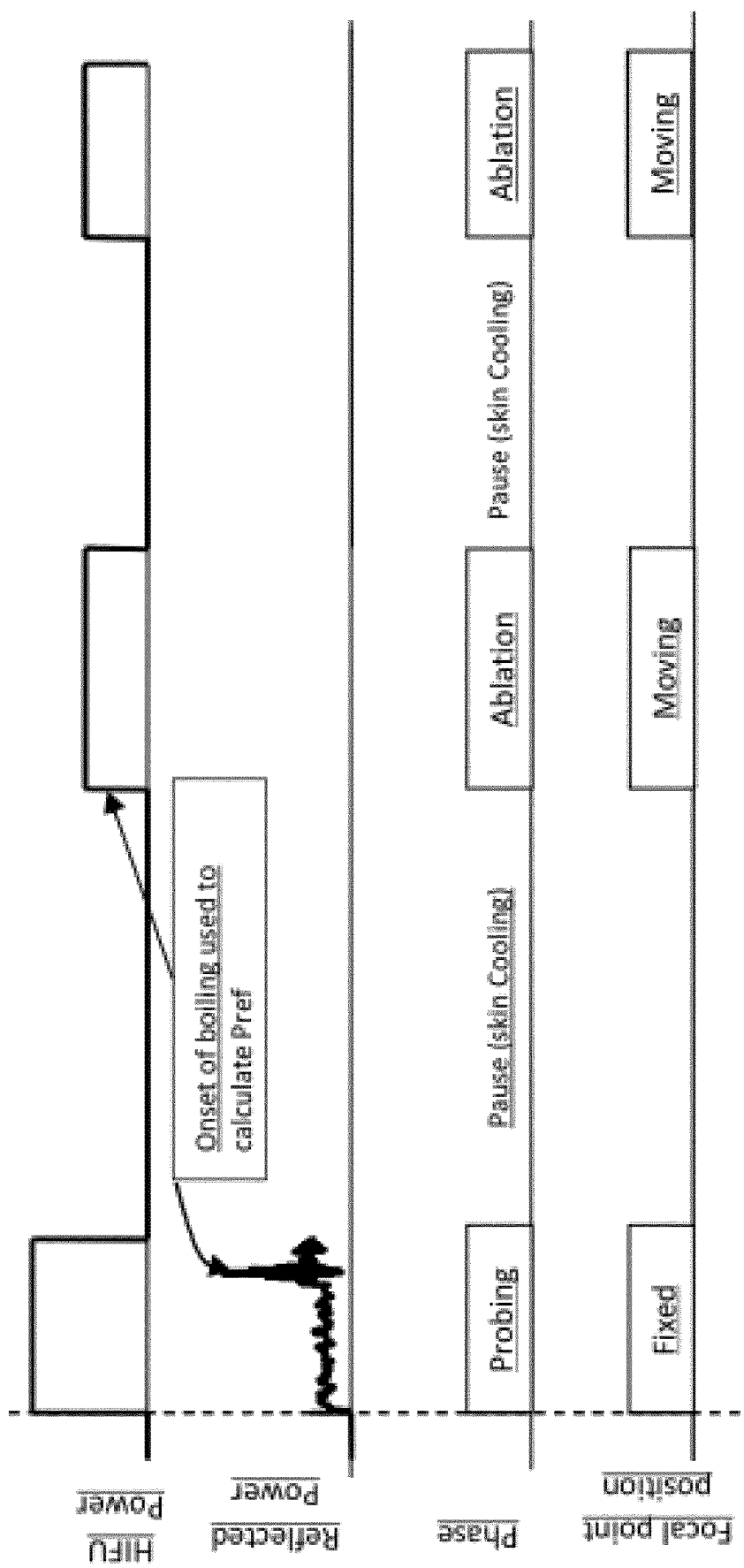

FIG. 4: A diagram of an alternative treatment cycle according to the invention.

Figure 5:
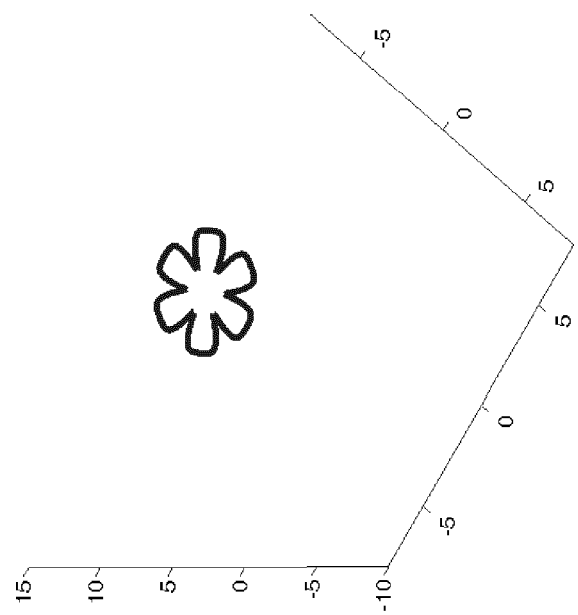
Figure 5:
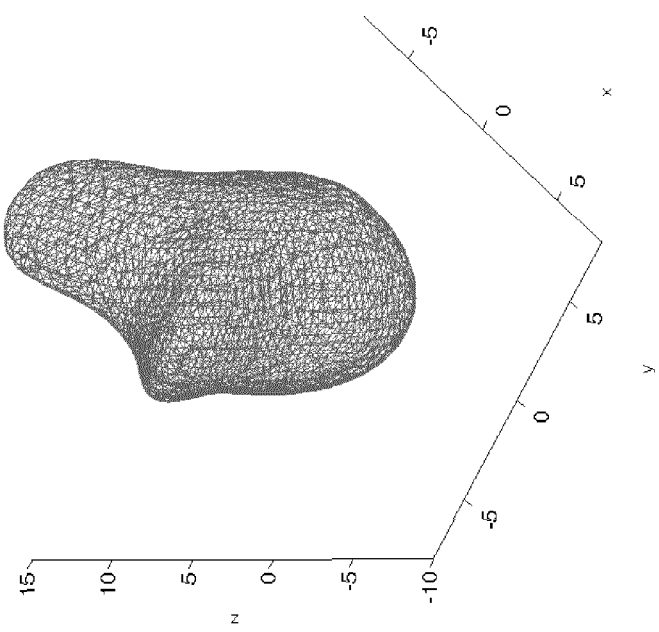

FIG. 5: A lesion created during treatment phase and the used trajectory.

Figure 6:
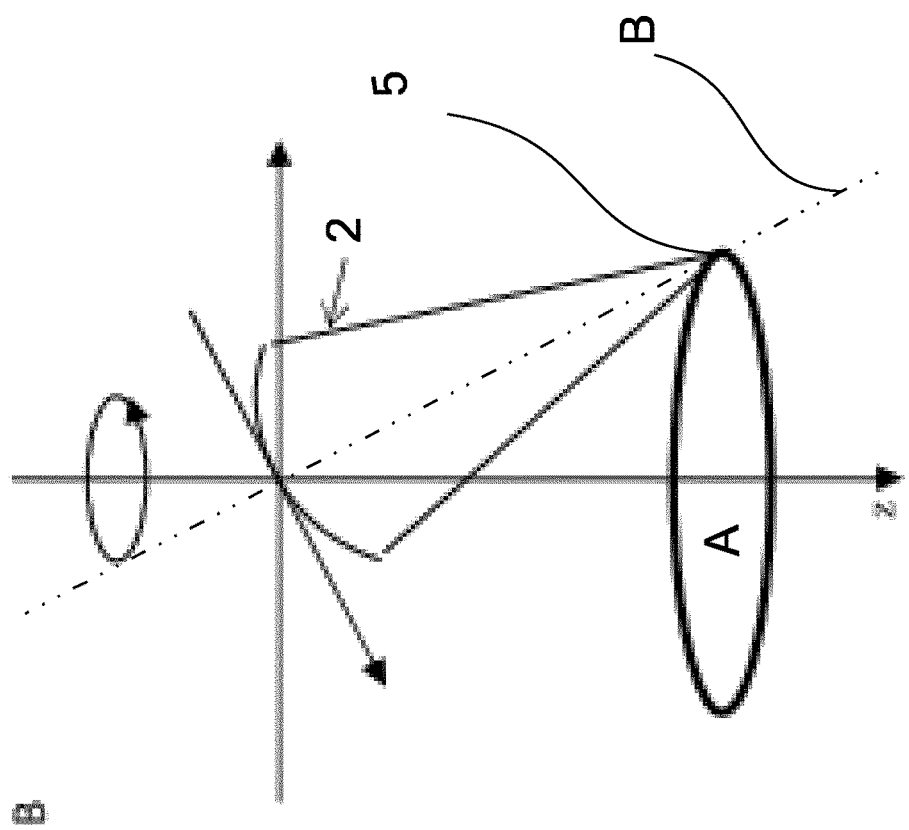
Figure 6:
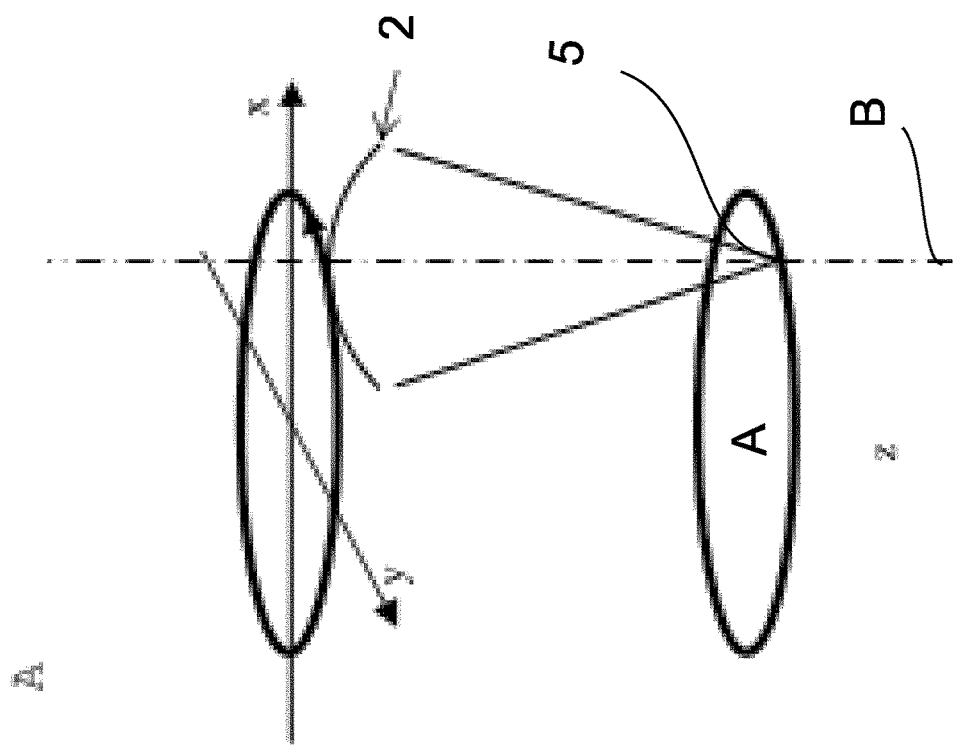

FIG. 6: Two moving options of the focal point during the treatment phase

FIG. 1 shows a schematic view of a device 1 according to the invention in a probing phase. The device comprises a treatment transducer 2. The treatment transducer 2 transmits HIFU pulses 3 of four seconds long and total acoustical power 80 Wa at transducer output on a target 4. In the probing phase as shown in FIG. 1, the HIFU pulses 3 have a focal point 5 on the target 4. The HIFU pulses 3 are transmitted to the target 4 until an detector 6 detects e.g., a hyperechoic mark in the tissue of the target 4.

Calculating means 7 in the form of a micro processor, which are connected to the detector 6 and to the transducer 2, determine the probing parameters necessary to achieve a change of tissue properties used by the treatment transducer 2 until the occurrence of hyperechoic marks, or a change in the reflected signal or an interference pattern. The calculating means 7 are further connected to the control 8 for controlling operation of the transducer 2. The control 8 defines treatment parameters for the treatment phase (see FIG. 2) based on the parameters calculated during the probing phase, which were used until hyperechoic marks occurred on the target 4. The control 8 further changes operation characteristics of the treatment transducer 2 by defocussing the HIFU pulses 3.

The whole process is performed by a computer program run on a processor unit 9.

Figure 2:
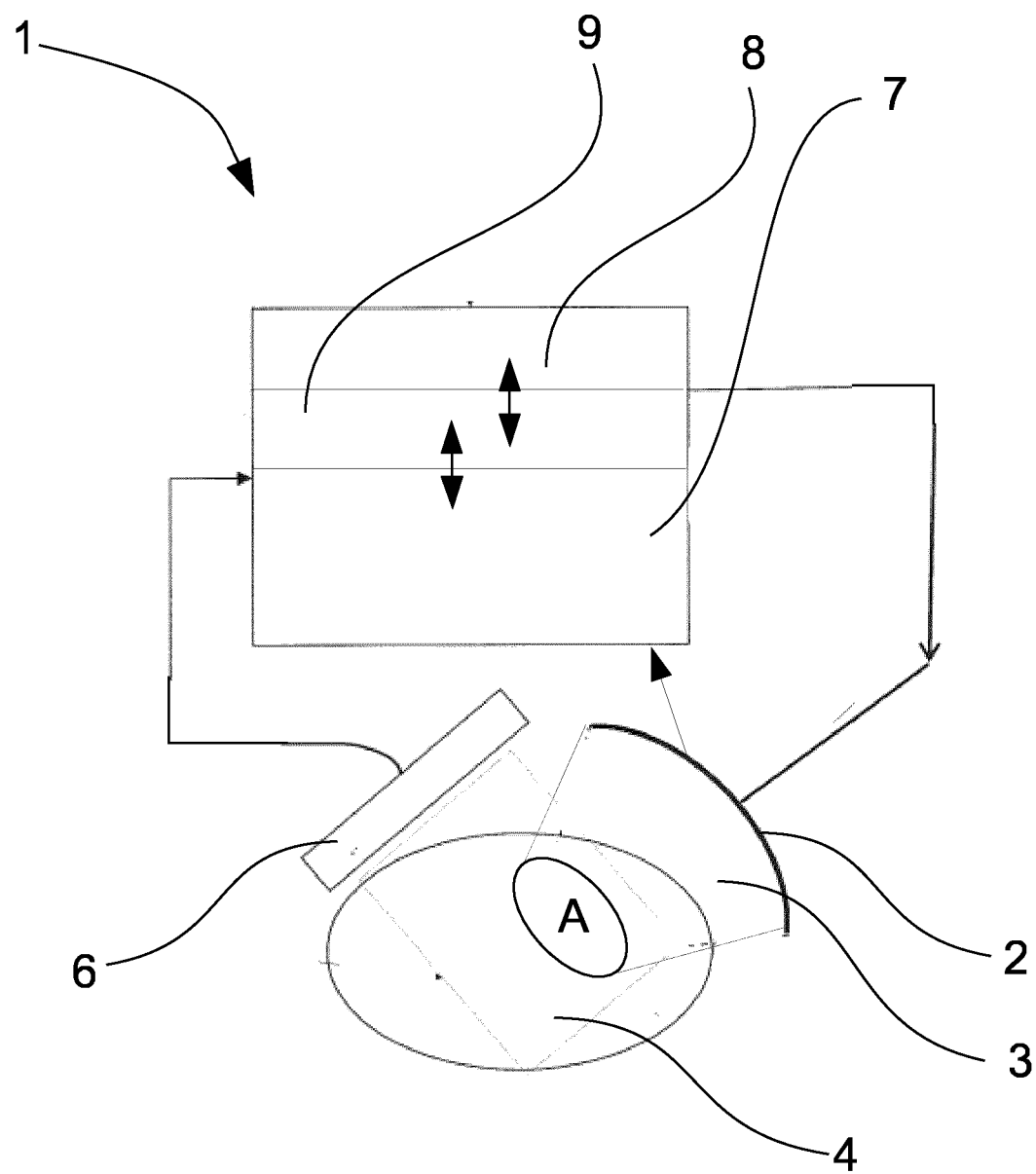

FIG. 2 shows the device 1 of FIG. 1 in a treatment phase. In the treatment phase, the HIFU pulses 3 transmitted by the transducer 2 are defocused by the control 8. Therewith, a larger area A of the target 4 is impinged by each HIFU pulse 3. The HIFU pulses in the treatment phase have a length of 0.12 seconds and transmitted with a total acoustical power of 60 Wa at transducer output being 75% of the power of the probing phase. The treatment transducer 2 typically transmits ten HIFU pulses 3 of 12 seconds to the target 4.

Afterwards, the control 8 changes the operation characteristics of the treatment transducer 2 back to those of the probing phase to reassess the parameters. The focal point 5 is then moved to another point on the target 4. The probing phase runs again until hyperechoic marks are detected by the detector 6. Afterwards, the control 8 changes again to the treatment phase with treatment characteristics. This cycle including a switching from the probing to treatment phase and back is run until the end of the treatment, e.g., until ablation of the whole target 4.

FIG. 3 shows a diagram of an alternative method according to the invention. In the probing phase, the focal point 5 is fixed and multiple of short HIFU pulses 3 of four seconds are delivered to the target 4. The pulses have a fixed 80 Wa. The occurrence of boiling, i.e. a hyperechoic mark is detected by the detector 6 because of a significant increase in reflected power. Once such a change in tissue properties is detected by the detector 6, the parameters are determined by the processor 7 and the control 8 will adjust the power of the transducer for a subsequent treatment phase ("ablation") 2. The adjustment is based on determined parameters of the probing phase calculated by calculating means 7. The adjusted power of the treatment phase is 75% of the power of the probing phase. Further, the control 8 moves the focal point 5 in a predetermined pattern by moving the transducer 2 during the pulses 3 of the treatment phase. These HIFU pulses 3 have a length of 24 seconds. After transmission of ten pulses 3 in the treatment phase, the transducer stops delivering further pulses 3 in order to let the skin of the patient cool. Afterwards, if the target is not yet completely ablated, a new probing phase might start followed by a treatment phase.

FIG. 4 shows a diagram for a further alternative method according to the invention. The power and duration of the pulses 3 in the probing phase are the same as in the method shown in FIG. 3. However, after a hyperechoic mark is detected by the detector 6 a pause is performed contrary to a direct change to the treatment phase as shown in FIG. 3. During the pause the skin of the patient can cool. After the pause, the treatment phase is started wherein the focal point 5 is moved in a predetermined pattern by the control 8. The pulses 3 in the treatment phase have the same duration and power as discussed above under FIG. 3. After a first pulse 3 of 12 seconds in the treatment phase, the control 8 induces again a pause to let the skin cool before control the transducer 2 to transmit a further pulse 3.

FIG. 5 shows on the left side a lesion created during the treatment phase according to the trajectory of the focal point pictured on the right side. As pictured, the movement of the focal point is daisy like.

FIG. 6 shows two different options in the situation where energy spreading is carried by mechanical means. In option A, a motorized system moving along Cartesian axes is used. In this situation the axis B of the transducer 2 stays parallel to the z axis. In the preferred embodiment of option B, the transducer tilts around θ (polar angle) and Φ (azimuthal angle), which results in less displacement of the transducer and better overall control. In this situation, the center of the transducer 2 stays at a fixed position, while the transducer axis tilts in order for the focus 5 to travel along focal point path. In both cases, a movement along z axis can be added to create lesions of different heights.

Table 1 compares a method of the invention (labelled as "fast scanning") to a pulse and pause method known from the state of the art (labelled as "legacy"). As shown the volume of each individual lesion can be increased by a factor of more than 10. To represents the time of the pulses during the treatment. 'To', is the time used for cooling between the pulses. The pulse and pause method does not have a probing phase. Therefore, no time is shown for the "legacy" method in the probing phase. Height, diameter and individual lesion volume represent the size of the target that is coagulated by each treatment pulse.

Probing time=$T_{on}+T_{off}$ of the probing pulse

Probing Duty cycle: represents the frequency of probing relative to the treatment phase, here one probing every 10 treatment pulses.

Volumetric rate=rate of ablation which takes into account the increase in treatment duration caused by the probing phase.

Table 2 discloses the same method as table 1 but uses alternative parameters for the "fast scanning". With the alternative parameters, the volume of each individual lesion can still be increased by a factor of more than 6.

TABLE 1

|  | 'Fast Scanning' | 'Legacy' | unit |
| --- | --- | --- | --- |
| height | 17 | 9 | mm |
| diameter | 4.5 | 1.9 | mm |
| individual lesion volume | 270 | 26 | mm3 (cylinder) |
| Ton | 12 | 4 | s |
| Toff | 30 | 15 | s (cooling between pulses) |
| Probing time | 20 | N/A | s |
| Probing Duty cycle | 10 | N/A |  |
| Volumetric rate | 6.1 | 1.3 | (mm3/sec) |

TABLE 2

|  | 'Fast Scanning' | 'Legacy' | unit |
| --- | --- | --- | --- |
| height | 8 | 9 | mm |
| diameter | 5 | 1.9 | mm |
| individual lesion volume | 157 | 26 | mm3 (cylinder) |
| Ton | 12 | 4 | s |
| Toff | 30 | 15 | s (cooling between pulses) |
| Probing time | 20 | N/A | s |
| Probing Duty cycle | 10 | N/A |  |
| Volumetric rate | 4.5 | 1.3 | (mm3/sec) |

The invention claimed is:

1. A device for therapeutic treatment comprising:
HIFU transducer for generating and transmitting HIFU pulses to a target, the HIFU transducer being operable in at least a probing mode, during a probing phase, and in a treatment mode, during a treatment phase,
    wherein in the probing phase, the HIFU transducer is operated with at least one probing operation characteristic, said operation characteristic including emission of a pulse with a focal point, and
    in the treatment phase, the HIFU transducer is operated with at least one treatment operation characteristic different from the probing operation characteristic,
a detector designed to detect a change of tissue properties caused by said HIFU pulses in the target during said probing phase,
calculating means for determining at least one probing parameter necessary to achieve said change of tissue properties detected by the detector during the probing phase
a control for defining said treatment parameters on a basis of said at least one probing parameter,
said control is further designed to change the operation characteristics, from the probing phase to the treatment phase, by increasing an area on the target of at least one pulse impinged by said HIFU pulse during the treatment phase, and by generating pulses in the treatment phase that are longer in duration than in the probing phase.

2. The device according to claim 1, wherein said control is designed to increase the area on the target impinged by said HIFU pulse by defocussing the HIFU pulses.

3. The device according to claim 1, wherein said control is designed to increase the area on the target impinged by said HIFU pulse by moving said focal point over the target.

4. The device according to claim 3, wherein said control is designed to move said focal point in a predefined trajectory, such that at least one point on the target is impinged more often than remaining points on the trajectory.

5. The device according to claim 1, wherein the calculating means are designed to estimate parameters including at least one of a duration of HIFU pulses and a power of HIFU pulses.

6. The device according to claim 1, wherein during the probing phase said control is designed to generate HIFU pulses having a length of 2 to 8 seconds.

7. The device according to claim 1, wherein during the treatment phase said control is designed to generate HIFU pulses having a length of at least one of 8 to 30, 8 to 10 and 10 to 30 seconds.

8. The device according to claim 1, wherein said control of the device is designed to set a power of the transducer, during the treatment phase, to less than 100% of a power of the transducer during the probing phase necessary to achieve the change of tissue properties in the target detected by the detector.

9. The device according to claim 1, wherein the transducer is toroidal and set to form a torpid HIFU beam, where the beam is concentrated onto a ring focus.

10. A method of controlling a therapeutic treatment device comprising the steps of:
   detecting, with an detector, changes of tissue properties caused by HIFU waves emitted by a HIFU transducer operated during a probing phase with probing operation characteristics,
   determining at least one probing parameter necessary to achieve said change of tissue properties detected by the detector during the probing phase,
   defining treatment parameters for a treatment phase based on said probing parameters,
   changing the operation characteristics, from the probing phase to the treatment phase, by increasing an area of at least one pulse on a target impinged by said HIFU pulse during the treatment phase, and by generating pulses in the treatment phase that are longer in duration than in the probing phase.

11. The method according to claim 10, wherein the area on the target impinged by said HIFU pulse is increased by defocussing the HIFU pulses of the HIFU transducer.

12. The method according to claim 10, wherein the area on the target impinged by said HIFU pulse is increased by moving a focal point of the HIFU pulses of the HIFU transducer over the target.

13. A computer program product comprising software code portions for performing the method according to claim 10, when the product is run on a computer.

14. A method of treating tissue with HIFU from a therapeutic treatment device, the method comprising:
   emitting HIFU waves with defined parameters with a HIFU transducer operated with probing operation characteristics, during a probing phase,
   detecting, with a detector, changes of tissue properties caused by the emitted HIFU waves,
   determining at least one probing parameter necessary to achieve said change of tissue properties, detected by the detector, during the probing phase,
   defining treatment operation characteristics for a treatment phase based on said probing characteristic
   changing the operation characteristics from the probing phase to the treatment phase by increasing an area of at least one pulse on a target impinged by said HIFU pulse, and by generating pulses in the treatment phase that are longer in duration than in the probing phase, and
   emitting HIFU waves with defined parameters during said treatment phase.

15. The method according to claim 14, wherein the area on the target impinged by said HIFU pulse is increased by defocussing the HIFU pulses of the HIFU transducer.

16. The method according to claim 14, wherein the area on the target impinged by said HIFU pulse is increased by moving a focal point of the HIFU pulses of the HIFU transducer over the target.

17. A computer program product comprising software code portions for performing the method according to claim 14, when the product is run on a computer.

18. The method of claim 14, wherein the device comprises:
   the HIFU transducer generating and transmitting HIFU pulses to a target, the HIFU transducer being operable in at least a probing mode, during a probing phase, and in a treatment mode, during a treatment phase,
      wherein in the probing phase, the HIFU transducer is operated with at least one probing operation characteristic, said operation characteristic including emission of a pulse with a focal point, and
      in the treatment phase, the HIFU transducer is operated with at least one treatment operation characteristic different from the probing operation characteristic,
   a detector designed to detect a change of tissue properties caused by said HIFU pulses in the target during said probing phase,
   calculating means for determining at least one probing parameter necessary to achieve said change of tissue properties detected by the detector during the probing phase
   a control for defining said treatment parameters on a basis of said at least one probing parameter,
   said control is further designed to change the operation characteristics, from the probing phase to the treatment phase, by increasing an area on the target of at least one pulse impinged by said HIFU pulse during the treatment phase, and by generating pulses in the treatment phase that are longer in duration than in the probing phase.

19. The method of claim 10, wherein the device comprises:
   the HIFU transducer generating and transmitting HIFU pulses to the target, the HIFU transducer being operable in at least a probing mode, during a probing phase, and in a treatment mode, during a treatment phase,
      wherein in the probing phase, the HIFU transducer is operated with at least one probing operation characteristic, said operation characteristic including emission of a pulse with a focal point, and
      in the treatment phase, the HIFU transducer is operated with at least one treatment operation characteristic different from the probing operation characteristic,
   a detector designed to detect a change of tissue properties caused by said HIFU pulses in the target during said probing phase,
   calculating means for determining at least one probing parameter necessary to achieve said change of tissue properties detected by the detector during the probing phase
   a control for defining said treatment parameters on a basis of said at least one probing parameter,
   said control is further designed to change the operation characteristics, from the probing phase to the treatment phase, by increasing an area on the target of at least one pulse impinged by said HIFU pulse during the treatment phase and by generating pulses in the treatment phase that are longer in duration than in the probing phase.

* * * * *